United States Patent
Rohlman

(10) Patent No.: US 10,485,751 B2
(45) Date of Patent: Nov. 26, 2019

(54) ANTI-SOAP FORMULATION

(71) Applicant: Rachel Rohlman, Alachua, FL (US)

(72) Inventor: Rachel Rohlman, Alachua, FL (US)

( * ) Notice: Subject to any disclaimer, the term of this patent is extended or adjusted under 35 U.S.C. 154(b) by 155 days.

(21) Appl. No.: 15/807,991

(22) Filed: Nov. 9, 2017

(65) Prior Publication Data

US 2019/0133921 A1    May 9, 2019

(51) Int. Cl.
*A61K 36/00* (2006.01)
*A61K 8/92* (2006.01)
*A61Q 19/10* (2006.01)

(52) U.S. Cl.
CPC ............ *A61K 8/922* (2013.01); *A61Q 19/10* (2013.01)

(58) Field of Classification Search
CPC ..................................................... A61K 36/00
See application file for complete search history.

(56) References Cited

U.S. PATENT DOCUMENTS

| 2007/0141017 A1* | 6/2007 | Horska | A61K 8/922 424/74 |
| 2014/0378363 A1* | 12/2014 | Thiessies | C11D 3/126 510/151 |

FOREIGN PATENT DOCUMENTS

| CN | 105219559 | 1/2016 |
| CN | 105543017 | 5/2016 |
| KR | 20110088799 | 8/2011 |

OTHER PUBLICATIONS

No reference is cited.*

* cited by examiner

Primary Examiner — Qiuwen Mi
(74) Attorney, Agent, or Firm — David L. King

(57) ABSTRACT

An anti-soap formulation has at least 50 percent or more Hemp oil. The anti-soap formulation further has one or more ingredients selected from the group of Jojoba oil, Babassu oil, Squalane, Castor oil, Red Raspberry seed oil, or any other moisturizing oil or fragrance producing oil. The anti-soap formulation preferably includes two or more selected from the group of Jojoba oil, Babassu oil, Squalane, Castor oil, Red Raspberry seed oil, or any other moisturizing oil or fragrance producing oil. Ideally, the anti-soap formulation includes 10 percent or more Jojoba oil, 5 percent or more Babassu oil, 5 percent or more Squalane and 5 percent or more Castor oil.

12 Claims, No Drawings

ANTI-SOAP FORMULATION

TECHNICAL FIELD

This invention relates to a formulation of oils that cleanse the skin as well as moisturize that can be particularly beneficial the facial area as well as other parts of the body.

BACKGROUND OF THE INVENTION

It is well known that the repeated us of soaps and daily showers to clean oneself is a common practice in many cultures. The hot water and soap clean the body of dirt, sweat and odors, but also strip away the body's natural production of oils, the sebum, that moisturize and keep the skin soft and smooth. The result of this type of hygienic cleansing can be very harmful to the dermis layer resulting in drying and cracking of the skin and the premature onset of wrinkles.

To offset this, soap formulations and ingredients often try to incorporate skin moisturizing chemicals or features. This is a complex problem for soap's primary purpose of cleaning and removing of residues and oils on the skin surface.

In Asia, in particular, China, there have been recent attempts to add hemp extracts to soap. CN105543017, Sisal Hemp Soap, of Huang Guipeng dated May 4, 2016 teaches such a soap. CN105219559, Health Bath Soap Capable of Moistening Skin and Relieving Stress, assigned to Zhou Qingli, teaches the addition of a small amount of hemp seed oil in combination with other ingredients to make a bath soap.

In Korea 20110088799, A Method For Preparing A Soap And Body Cleanser Using By A Powdered Hemp Stem, is another example.

All of these compositions have a fatal flaw of the conflicting nature of soaps and the attempt to combine soap's oil stripping nature while simultaneously trying to leave a residue of protective oils on the skin.

The present invention recognizes this inherent conflict of moisturizing soaps and solves this by providing an Anti-Soap Formulation of a unique combination of oils that not only moisturize the skin, but effectively cleanse the skin.

Definitions

Hemp Oil—or hempseed oil is obtained by pressing hemp seeds. Cold pressed, unrefined hemp oil is dark to clear light green in color, with a nutty flavor. Refined hempseed oil is clear and colorless, with little flavor and lacks natural vitamins and antioxidants. Refined hempseed oil is primarily used in body care products.

Jojoba Oil—is the liquid produced in the seed of the *Simmondsia chinensis* (Jojoba) plant, a shrub, which is native to southern Arizona, southern California, and northwestern Mexico. The oil makes up approximately 50% of the jojoba seed by weight. The terms "jojoba oil" and "jojoba wax" are often used interchangeably because the wax visually appears to be a mobile oil, but as a wax it is composed almost entirely (~97%) of mono-esters of long-chain fatty acids and alcohols, accompanied by only a tiny fraction of triglyceride esters. This composition accounts for its extreme shelf-life stability and extraordinary resistance to high temperatures, compared with true vegetable oils.

Babassu oil—or cusi oil is a clear light yellow vegetable oil extracted from the seeds of the babassu palm (*Attalea speciosa*), which grows in the Amazon region of South America. It is a non-drying oil used in food, cleaners and skin products.

Squalane—is a hydrocarbon derived by hydrogenation of squalene. In contrast to squalene, due to the complete saturation of squalane, it is not subject to auto-oxidation. This fact, coupled with lower costs associated with squalane, make it desirable in cosmetic applications, where it is used as an emollient and moisturizer.

Squalene—is a natural 30-carbon organic compound originally obtained for commercial purposes primarily from shark liver oil (hence its name, as Squalus is a genus of sharks), although plant sources (primarily vegetable oils) are now used as well, including amaranth seed, rice bran, wheat germ, and olives. Yeast cells have been genetically engineered to produce commercially useful quantities of "synthetic" squalene. All plants and animals produce squalene as a biochemical intermediate, including humans. It occurs in high concentrations in the stomach oil of birds in the order Procellariiformes. Squalene is a hydrocarbon and a triterpene, and is a precursor for synthesis of all plant and animal sterols, including cholesterol and steroid hormones in the human body.

Castor Oil—is a vegetable oil obtained by pressing the seeds of the castor oil plant (*Ricinus communis*). Castor oil is a colorless to very pale yellow liquid with a distinct taste and odor once first ingested. Its boiling point is 313° C. (595° F.) and its density is 961 kg/m3. It is a triglyceride in which approximately 90 percent of fatty acid chains are ricinoleates. Oleate and linoleates are the other significant components.

Red Raspberry Seed Oil—is a rich source of polyunsaturated fats including omega 3, 6 and fatty acid, high in Vitamin E, especially tocotrienols and tocopherols and rich in Vitamin A Effectively moisturize and improve skin elasticity, reduces wrinkles, dryness and skin lines. It is regenerating skin cells. Red Raspberry Seed Oil is also the perfect choice for all of your bath, body, skin, and baby care, products where it offers excellent skin protection and will also help to stabilize, and improve the anti-oxidant activity. Red raspberry seed oil has a long shelf life due to its oxidative stability, making it an excellent oil for use in creams, lotions, lip balms, salves and other anhydrous formulations.

SUMMARY OF THE INVENTION

An anti-soap formulation has at least 50 percent or more Hemp oil. The anti-soap formulation further has one or more ingredients selected from the group of Jojoba oil, Babassu oil, Squalane, Castor oil, Red Raspberry seed oil, or any other moisturizing oil or fragrance producing oil. The anti-soap formulation preferably includes two or more selected from the group of Jojoba oil, Babassu oil, Squalane, Castor oil, Red Raspberry seed oil, or any other moisturizing oil or fragrance producing oil. Ideally, the anti-soap formulation includes 10 percent or more Jojoba oil, 5 percent or more Babassu oil, 5 percent or more Squalane and 5 percent or more Castor oil.

In one embodiment, the anti-soap formulation has at least 50 percent or more Hemp oil, 10 percent or more Jojoba oil, 5 percent or more Babassu oil, 5 percent or more Squalane, 5 percent or more Castor oil and 2 percent or more Red Raspberry seed oil.

In a more preferred embodiment, the anti-soap formulation has at least 60 percent Hemp oil, at least 15 percent Jojoba oil, at least 10 percent Babassu oil, at least 5 percent Squalane, at least 5 percent Castor oil and at least 2 percent Red Raspberry seed oil.

DETAILED DESCRIPTION OF THE INVENTION

The present invention is an anti-soap formulation that can be applied directly to the skin as a cleanser, more particularly, the face, to remove dirt and cosmetics such as makeup, eyeliner and lipstick. One rubs the anti-soap formulation onto the face and wipes it off with a hot moist cloth or towel, or alternatively, once the facial skin is cleaned, the formulation can be applied and left on the face for an extra moisturizing effect. The formulation is particularly useful in dry climates and regions where the face is exposed to dry conditions and excessive sun exposure such as found in skiing, boating or outdoor activities notorious for damaging the skin and causing premature aging and wrinkles.

The anti-soap formulation comprises a plurality of oils that are particularly useful in moisturizing the skin. The primary foundational oil is hemp oil which makes up at least half of the formulation. The hemp oil is preferably obtained from processing hemp seeds to obtain a hemp oil extract of high purity. A plurality of additional oils or non-soap compositions are then mixed with the hemp oil including two or more selected from a group of Jojoba Oil, Babassu Oil, Squalane, Castor Oil, Red Raspberry Seed Oil or Other Fragrance Based Oils Such As Black Cumin Seed Oil, Sunflower Oil, Avocado Oil, Essential Oils of Lavender, Geranium & Bergamot, and Vitamin E.

Preferably, the anti-soap formulation comprises at least 50 percent or more Hemp oil, 10 percent or more Jojoba oil, in combination with the other oils. More preferably, the anti-soap formulation has 50 percent or more Hemp oil, 10 percent or more Jojoba oil and 5 percent or more Babassu oil in combination with the other oils.

In a best mode of the present invention, the anti-soap formulation comprises: 60 percent Hemp oil, 15 percent Jojoba oil, 10 percent Babassu oil, 5 percent Squalane, 5 percent Castor oil, 2 percent Red Raspberry seed oil and 3 percent other oils.

It is understood these oils can be varied in amounts or one or more alternative oil substitutes can be used in place of the ingredients listed without departing from the spirit and scope of the invention which is to provide an anti-soap formulation comprising at least 50 percent or more Hemp oil mixed with one or more additional oils.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An anti-soap cleansing formulation comprises:
    a plurality of oils including a formulation of at least 50 percent or more Hemp oil and one or more selected from the group of Jojoba oil, Babassu oil, Squalane, Castor oil, or Red Raspberry seed oil; mixed with the Hemp oil forming a combination or mixture of the plurality of oils to cleanse and moisturize skin by applying the cleansing formulation onto the skin to remove dirt and cosmetics, and optionally once the skin is cleansed the cleansing formulation is applied and left on the skin, to moisturize the skin.

2. The anti-soap cleansing formulation of claim 1 includes two or more selected from the group of Jojoba oil, Babassu oil, Squalane, Castor oil, or Red Raspberry seed oil.

3. The anti-soap cleansing formulation of claim 1 wherein the formulation includes 10 percent or more Jojoba oil.

4. The anti-soap cleansing formulation of claim 1 further comprises 10 percent or more Jojoba oil, 5 percent or more Babassu oil and 5 percent or more Squalane.

5. The anti-soap cleansing formulation of claim 4 further comprises 5 percent or more Castor oil.

6. The anti-soap cleansing formulation of claim 1 wherein the plurality of oils further includes one or more fragrance based oils selected from the group of Black Cumin Seed Oil, Sunflower Oil, Avocado Oil, Essential Oils of Lavender, Geranium & Bergamot, and Vitamin E.

7. The anti-soap cleansing formulation of claim 2 wherein the formulation includes 10 percent or more Jojoba oil.

8. The anti-soap cleansing formulation of claim 2 wherein the plurality of oils further includes one or more fragrance based oils selected from the group of Black Cumin Seed Oil, Sunflower Oil, Avocado Oil, Essential Oils of Lavender, Geranium & Bergamot, and Vitamin E.

9. The anti-soap cleansing formulation of claim 3 wherein the formulation includes 5 percent or more Babassu oil.

10. The anti-soap cleansing formulation of claim 7 wherein the formulation includes 5 percent or more Babassu oil.

11. An anti-soap cleansing formulation comprises:
    at least 50 percent or more Hemp oil, 10 percent or more Jojoba oil, 5 percent or more Babassu oil, 5 percent or more Squalane, 5 percent or more Castor oil and 2 percent or more Red Raspberry seed oil.

12. An anti-soap cleansing formulation comprises:
    at least 60 percent Hemp oil, at least 15 percent Jojoba oil, at least 10 percent Babassu oil, at least 5 percent Squalane, at least 5 percent Castor oil and at least 2 percent Red Raspberry seed oil.

* * * * *